United States Patent [19]

Madding

[11] Patent Number: 5,521,313
[45] Date of Patent: May 28, 1996

[54] PROCESS FOR PREPARING CERTAIN AZAPIRONES

[75] Inventor: Gary D. Madding, Evansville, Ind.

[73] Assignee: Bristol-Myers Squibb Company, New York, N.Y.

[21] Appl. No.: 238,559

[22] Filed: May 5, 1994

[51] Int. Cl.$^6$ .................... C07D 403/12; C07D 403/14; C07D 241/04
[52] U.S. Cl. .................... 544/230; 544/231; 544/295
[58] Field of Search .................... 544/295, 230, 544/231

[56] References Cited

U.S. PATENT DOCUMENTS

| | | | |
|---|---|---|---|
| 3,717,634 | 2/1973 | Wu et al. | 544/230 |
| 4,351,939 | 9/1982 | Simms | 544/230 |
| 4,417,049 | 11/1983 | Sims | 544/231 |
| 4,423,049 | 12/1983 | Temple | 544/230 |
| 4,507,303 | 3/1985 | Ishizumi et al. | 544/230 |
| 4,524,206 | 6/1985 | New et al. | 544/230 |
| 4,892,943 | 1/1990 | Abou-Gharbia | 540/575 |
| 5,227,486 | 7/1993 | Merce-Vidal et al. | 544/295 |

*Primary Examiner*—Matthew V. Grumbling
*Attorney, Agent, or Firm*—Richard P. Ryan

[57] ABSTRACT

An improved process for preparation of certain useful azapirones, e.g. buspirone, gepirone, tandospirone, etc., comprises the reaction of a novel spiroquaternary piperazinium hydroxide with an appropriate imide to form imidate salts which are then converted to the azapirone by heating. This process is suitable for large scale adaptation and has advantages in greater safety and efficiency.

16 Claims, No Drawings

PROCESS FOR PREPARING CERTAIN AZAPIRONES

BACKGROUND OF THE INVENTION

This invention describes an improved, commercializable process for the synthesis of certain useful azapirone compounds. "Azapirone" is a term that has been used to describe a structural class of psychotropic compounds that demonstrate similar pharmacology relating to interaction with monoaminergic pathways in particular brain regions.

The azapirones amenable to the new process of this invention can be shown by some representative illustrations of certain azapirone drug agents having structural formula (I).

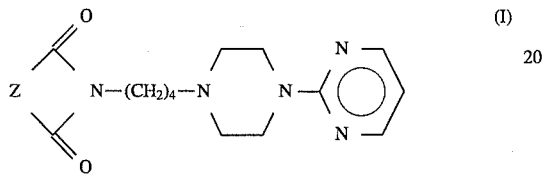
(I)

Perhaps the best known representative of the azapirone class of psychotropic agents is buspirone (1), originally disclosed in U.S. Pat. No. 3,717,634.

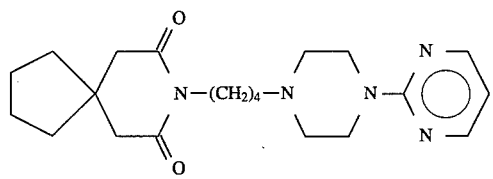
(1)

Some other well known members are:
gepirone, where Z is

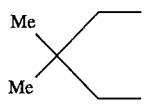

(U.S. Pat. No. 4,423,049);
tandospirone, where Z is

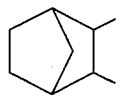

(U.S. Pat. No. 4,507,303); and
WY-47,846, where Z is

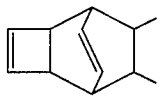

(U.S. Pat. No. 4,892,943).

While a number of synthetic processes have been disclosed for the synthesis of these azapirones, a method of choice, currently used for large scale preparation of buspirone, was disclosed by Sims in U.S. Pat. No. 4,351,939. The Sims method involves the reaction of a spiro-substituted glutarimide (3) with a novel spiroquaternary ammonium halide (4) to yield buspirone or

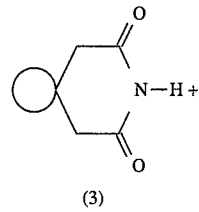
(3)

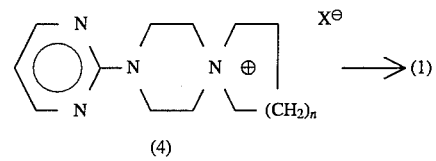
(4)

a close analog. The halide, X, is preferably bromide. The reaction is carried out in a hot inert reaction medium in the presence of a strong base. In practice, the reaction process involves a biphasic reaction of (3) and (4) in refluxing xylene with solid potassium carbonate.

For scale-up, this prior art synthesis suffers from several processing disadvantages including high temperature processing of toxic solvents, a biphasic reaction mixture requiring highly efficient stirring, and the presence of inorganic by-products.

In contrast, the improved process proceeds via an imidate salt, free of inorganic by-products, and convertible in high yield to the desired azapirone upon gentle heating. There is nothing in the Sims process or other background art that would suggest the novel process and imidate salt intermediates of the present invention.

SUMMARY OF THE INVENTION

This invention relates to a new, improved process for the preparation of certain useful azapirone psychotropic agents such as buspirone, gepirone, tandospirone, WY 47,846, and structural analogs. The process employs a novel spiroquaternary piperazine hydroxide starting material and proceeds through novel spiroquaternary imidates to azapirones under mild conditions resulting in high yields of product without inorganic by-product contamination.

DETAILED DESCRIPTION OF THE INVENTION

The following flowchart, Scheme I, illustrates the preparation of certain azapirones utilizing the instant process.

Scheme I

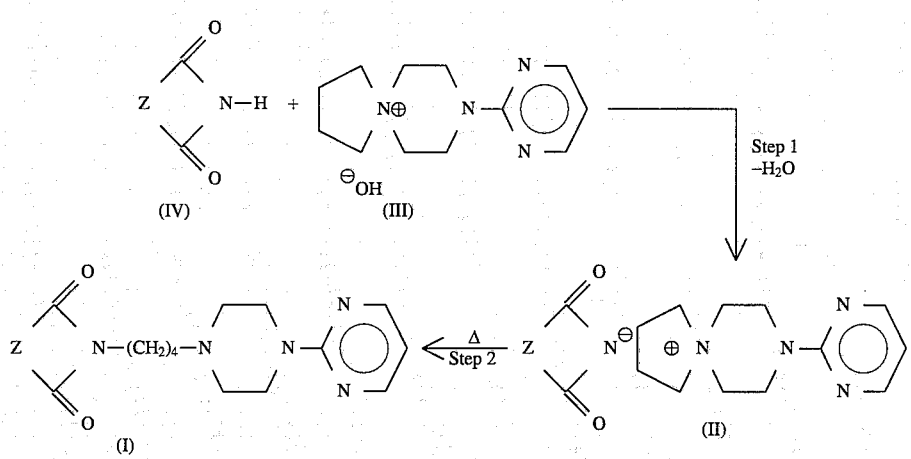

The first step of the process outlined in Scheme I involves starting with a novel spiroquaternary piperazine hydroxide (III), specifically 8-(2-pyrimidinyl)- 8-aza-5-azoniaspiro[4,5]decane hydroxide. This compound is prepared in a straightforward manner by an ion-exchange process utilizing the Sims spiroquaternary piperazine bromide (V).

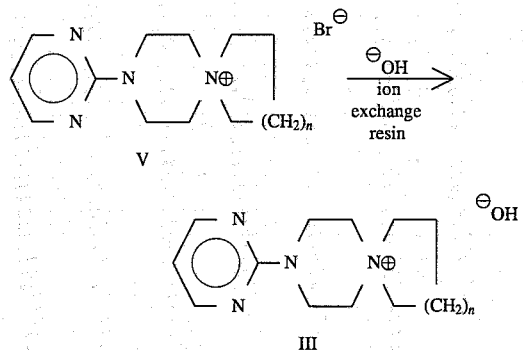

Selection of the hydroxide (III) as a starting material in this novel process allows the process to be salt-free, thereby eliminating an inorganic contaminant that is often troublesome to remove completely.

Since III is not stable isolated as an oil, it is more practical to bypass its isolation. Eluant methanol containing freshly prepared III from the ion exchange column is therefore run directly into a vessel containing solid imide (IV). When elution of III from the column is completed, the methanolic solution of III and IV is concentrated in vacuo to provide a novel spiroquaternary imidate salt (II). These novel salts are convertible into a desired azapirone product (I) by step 2 which comprises gentle heating. The II imidates may be heated in the solid state in order to convert II to I but heating in organic solvents is preferred. Among solvents, higher boiling, non-protic solvents generally give higher yields of azapirone in shorter heating times. Protic solvents do not provide as clean or as complete conversions, due perhaps to competing solvolysis reactions.

Since the spiroquaternary imidate salts are generally hygroscopic, they are generally not isolated but are taken on to I by heating the salt, II, in a nonprotic organic solvent such as THF, acetonitrile, toluene, N-methylpyrrolidinone, methylisobutyl ketone, and the like.

The process of the instant invention has several advantages for large scale production of useful azapirones. Since neither isolation nor purification of III or II is necessary, and because the process proceeds without the concomitant generation of any salt by-products, less materials handling and processing are required. In particular, the filtration of a hot reaction mixture in a solvent such as xylene, as done in the Sims process, is a troublesome procedure for large scale manufacture. The elimination of a solid acid scavenging reagent such as potassium carbonate in the improved process removes mixing problems that result from large scale biphasic reaction mixtures.

In prior art processes, such as the Sims process, the azapirone base is not isolated by crystallization but instead by acid-extraction followed by precipitation of the azapirone by basification of the extracts and finally, the product is obtained by filtration. In the improved instant process, however, azapirone base is obtainable in high yield and purity by simple crystallization.

In sum, the instant process features the coupling of a novel spiroquaternary piperazinium hydroxide (III) and various imides (IV) to conveniently form azapirone drug products under mild conditions and in high yield and purity. By-products formed in prior art high temperature processes are avoided and product isolation is facilitated. With elimination of certain process features and operations required in prior art processes, the novel improved azapirone process provides additional safety and handling advantages.

DESCRIPTION OF SPECIFIC EMBODIMENTS

The process of this invention is illustrated in greater detail by the following examples directed to preferred embodiments of the process steps generally described hereinabove. These examples, however, should not be construed as limiting the scope of the present invention in any way.

EXAMPLE 1

8-(2-Pyrimidinyl)-8-aza-5-azoniaspiro[4.5]decane Hydroxide (III)

A glass column (2.3 cm O.D.×50 cm) was charged with 250 mL wet Dowex 1X8-50 ion-exchange resin (Cl⁻). The column was back-washed with deionized water until the wash had pH 7 and gave a negative silver nitrate test. It was then back-washed with 10 wt % NaOH (the resin floated) until the effluent (after acidification with nitric acid) gave a negative silver nitrate test. It was then back-washed with deionized water to pH 7, and then with 4 L methanol.

A solution of 49.7 g (0.166 mole) 8-(2-pyrimidinyl)-8-aza-azoniaspiro[4.5]decane bromide V (50% of the exchange capacity of the column) in 1600 mL methanol was prepared. The reported relative selectivity coefficients[1] are 0.09 for hydroxide, 1.00 for chloride and 2.8 for bromide, i.e. bromide binds 31.1 times more tightly to the polymer than does hydroxide. The methanol solution was passed down through the column over 3 h. As the solution passed, the column became lighter in color from the top down, and by the time the solution had been passed, approximately 0.4 of the column had changed color. The column was eluted with an additional 500 mL methanol. The combined eluants were concentrated in vacuo to 70 g of amber oil. This material was dissolved in 300 mL THF; the resulting mixture was filtered to remove a small amount of insoluble material. The filtrate was dried over Molecular Sieve 4A and again concentrated in vacuo to give 49.4 g (125.7% of theory) clear brown oil. An aqueous solution had pH 13 and, after acidification with $HNO_3$, gave a negative silver nitrate test. Hplc analysis[2] showed a single major peak with a retention time equal to that of the starting material. The two salts would be expected to give identical retention times in this phosphate buffered system. A 0.3353 g sample in 100 mL water was titrated to a phenolphthalein end-point with 9.32 mL (0.932 mmole) 0.2 N HCl. Therefore, the sample contained 0.932 mmole titratable base, presumably as the title compound (0.22 g), indicating that the brown oil contained 65.7 wt% of the spiroquaternaryammonium hydroxide. The total oil then contained 0.657×49.4 g=32.5 g of the desired material (82.6% of theory).

[1] *Amberlite Ion Exchange Resins*, Laboratory Guide, Rohm and Haas 6.
[2] (Waters C18 m-Bondapak 3.9 mm×30 cm, 1.5 mL/min of 25% (vol) MeCN: 75% (vol) 0.05M $KH_2PO_4$ at pH 5.4).

EXAMPLE 2

8-(2-Pyrimidinyl)-8-aza-5-azoniaspiro[4.5]decane, salt with 4,4-Dimethyl-2,6-piperidinedione (1:1) (II)

Compound II may also be referred to as 8-(2-pyrimidinyl)- 8-aza-5-azoniaspiro[4.5]decane 3,3-dimethylglutarimidate.

The ion-exchange column as previously described (Example 1) was converted to the hydroxide form; the water content of the last of the methanol column wash was 0.35 wt % (Mitsubishi Moisture Meter CA06). A solution of 49.7 g (0.166 mole) of the Formula V compound, 8-( 2-pyrimidinyl)-8-aza-5-azoniaspiro[4.5]decane bromide in 500 mL methanol was passed down through the column over 2 h, and the eluant was collected in an argon-purged flask containing 23.4 g (0.166 mole) 3,3-dimethyl-glutarimide (IV). The mixture was stirred and, as the elution neared completion, all the solid dissolved. The water-clear solution was concentrated in vacuo at ≦25° C. to give a solid, which was slurried with 200 mL THF and again concentrated. An hplc[2] analysis of the residual solid showed curves at 210 and 238 nm which would be equivalent to an equimolar mixture of compounds IV and V, as expected assuming the salt of the two was dissolved in a pH 5.4 buffer. The solid remaining after removal of the THF was stirred 1 h with 500 mL THF and then collected on a filter. The filter-cake was rinsed with 150 mL THF and then quickly transferred to a vacuum oven. Traces of solid left on the filter paper, with exposure to the room air, quickly became sticky and liquefied, indicating the solid was hygroscopic. The bulk solid was stored in vacuo (15 mm Hg) for 1 h, and then transferred to a tightly-capped amber bottle. It was a white, finely-divided, free-flowing solid. A 0.0941 g sample of the crystalline solid exposed to room air for 5 h gained 0.0101 g (of water); the mole ratio of water to compound calculated to be 2.15. A sample of the bulk had mp 143°–145° C. (hot-stage apparatus, between microscope cover slips). The melting point sample was further heated to 150° C. and held for about 1 min. Hplc analysis[2] showed conversion to a nearly pure sample of the corresponding azapirone product.

Calc. (found) for $C_{19}H_{29}N_5O_2$:C 63.49 (60.42), H 8.13 (8.42), N 19.48 (17.37). Ir, $^1H$ NMR and $^{13}C$ NMR were consistent for the assigned structure.

A two-dimensional COSY NMR spectrum allowed the assignment of all the protons of the imidate salt as shown below.

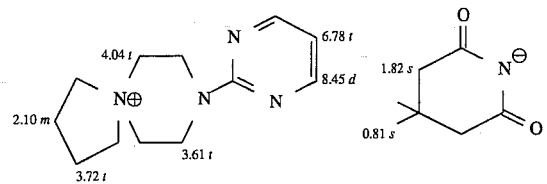

EXAMPLE 3

8-(2-Pyrimidinyl)-8-aza-5-azoniaspiro[4.5]decane, salt with 8-Azaspiro[4.5] decane-7,9-dione (1:1) Hydrate (II)

Analogous to the procedure of Example 2, a solution of 29.9 g (0.10 mole) of the decane bromide compound V in methanol was converted to the hydroxide form, which was immediately reacted with 8-azaspiro[4.5]decane-7,9-dione (IV) to produce an imidate salt as a hygroscopic crystalline compound in 88.7% yield. Calc. (found) for $C_{21}H_{31}N_5O_2$: C 65.43 (60.39), H 8.11 (7.81), N 18.17 (16.20). Calc. (found) for $C_{21}H_{31}N_5O_2 \cdot 1.75\ H_2O$: C 60.48 (60.39), H 8.34 (7.81), N 16.79 (16.20). The ir, $^1H$ NMR and $^{13}C$ NMR spectra were consistent for the assigned structure.

By analogy to the Example 2 imidate, the following proton assignments are made:

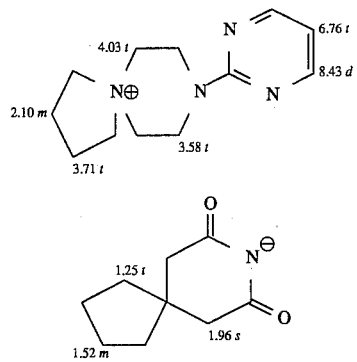

EXAMPLE 4

8-(2-Pyrimidinyl)-8-aza-5-azoniaspiro[4.5]decane, salt with (endo,endo)-Bicyclo[2.2.1]heptane-2,3-dicarboxylic acid imide (II)

A glass column (2.3 cm O.D.×50 cm) was charged with 250 mL wet Dowex 1X8-50 ion-exchange resin (Cl⁻). The column was back-washed with deionized water until the wash had pH 7 and gave a negative silver nitrate test. It was then back-washed with 10 wt % NaOH (the resin floated) until the effluent (after acidification with nitric acid) gave a negative silver nitrate test. It was then back-washed with deionized water to pH 7, and then with 4 L methanol; the water content of the last of the methanol column wash was 0.35 wt % (Mitsubishi Moisture Meter CA06).

A solution of 1.65 g (0.010 mole) (endo,endo)bicyclo [2.2.1]heptane-2,3-dicarboxylic acid imide (IV) in 20 mL methanol was prepared and filtered with a 0.45 m syringe filter. Another solution of 2.99 g (0.010 mole) 8-(2-pyrimidinyl)-8-aza-5-azoniaspiro[4.5]decane bromide (V) in 30 mL methanol was passed through the Dowex column over 45 min. The column effluent was collected into an argon-purged flask containing the solution of the imide. The reaction solution was stirred during the elution and collection. The column was rinsed with 300 mL methanol.

The resulting methanol solution was concentrated in vacuo ≦20° C. to give a thick oil. The residue was twice slurried with 25 mL tetrahydrofuran and concentrated in vacuo. The resultant thick oil was stored in vacuo (15 torr) at 23° to 25° C. for 24 h. Upon scratching with a spatula the oil crystallized. A few seeds were retained and the bulk of the material was dissolved in 50 mL methanol. The solution was concentrated in vacuo at ≦20° C. to a thick syrup. The syrup was stirred with 100 mL tetrahydrofuran and the seed crystals. The product crystallized. It was collected on a filter, and then it was dried in vacuo (15 torr) for 3 h at 23° C. The white free-flowing powder weighed 2.82 g. The analytical data (ir, $^1$H NMR and $^{13}$C NMR and elemental analysis) were consistent for the imidate salt containing 1.5 equivalents of water.

Calc. (found) for $C_{21}H_{29}N_5O_2 \cdot 1.5\ H_2O$: C 61.44 (61.65); H 7.86 (7.55); N 17.06 (17.01). $^1$H NMR (200 MHz, $d_6$-DMSO) δ8.48 (d, J=6 Hz, 2H), 6.80 (t, J=6 Hz, 1H), 4.07 (bs, 4H), 3.70 (m, 4H), 3.58 (t, 4H), 3.47 (s, 3H), 2.55 (s, 2H), 2.24 (s, 2H), 2.11 (bs, 4H), 1.40 (s, 2H), 1.22 (bq, 4H). $^{13}$C NMR (50 MHz, $d_6$-DMSO) δ195.0, 161.0, 158.5, 111.6, 61.43, 57.72, 53.29, 47.13, 38.78, 38.10, 24.83, 20.78.

EXAMPLE 5

8-[4-[4-(2-Pyrimidinyl)-1-piperazinyl]butyl]-8-azaspiro[4.5]decane-7,9-dione Buspirone (I)

A suspension of 11.1 g (28.8 mmole) of the imidate salt of Example 3 in 50 mL 4-methyl-2-pentanone was stirred and heated to gentle reflux under argon; the solid slowly dissolved. After 45 rain heating, tlc[3] showed a major spot at $R_f$0.6 and a minor spot at the origin. The reaction solution was filtered to remove a very small amount of insoluble material. The filtrate was chilled in an ice bath, and it was seeded with a crystal of buspirone. A precipitate began to form immediately. The mixture was chilled and stirred for 1 h. The resulting solid was collected on a filter, rinsed with 2×5 mL 4-methyl-2-pentanone and air-dried. The white solid weighed 7.6 g. The filtrate was concentrated by distillation to 20 mL and chilled to obtain a second crop. The off-white solid weighed 1.3 g. Total 8.9 g (80.2% of theory), hplc[2] HI[4]94.3% for buspirone. Calc. (found) for $C_{21}H_{31}N_5O_2$: C 65.43 (65.41), H 8.11 (8.22), N 18.17 (17.89).

[3] " MKGF silica, 9 $CH_2Cl_2$:1 MeOH, u.v.
[4] HI is the homogeneity index as determined by hplc.

EXAMPLE 6

3,3-Dimethyl-1-[4-[4-(2-pyrimidinyl)-1-piperazinyl]butyl]glutarimide Gepirone (I)

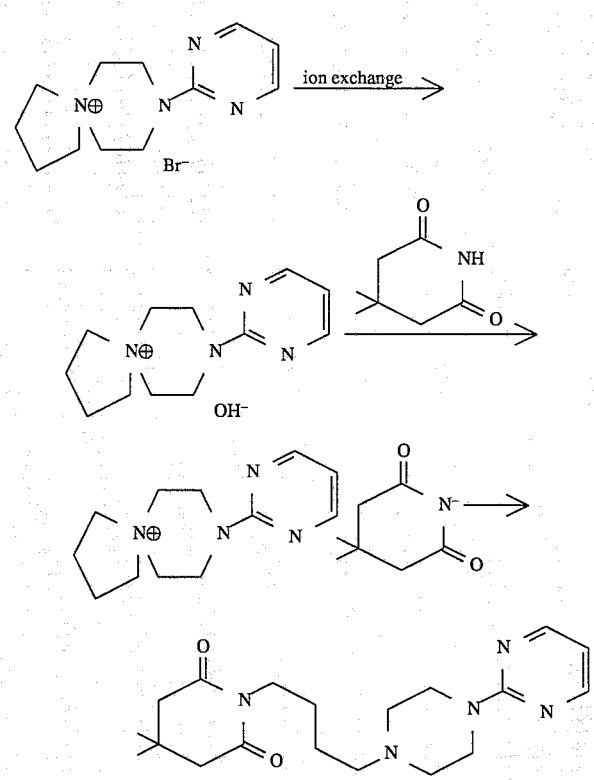

A glass column (2.3 cm O.D.×50 cm) was charged with 250 mL wet Dowex 1X8-50 ion-exchange resin (Cl$^-$). The column was back-washed with deionized water until the wash had pH 7 and gave a negative silver nitrate test. It was then back-washed with 10 wt % NaOH (the resin floated) until the effluent (after acidification with nitric acid) gave a negative silver nitrate test. It was then back-washed with deionized water to pH 7, and then with 4L methanol; the final effluent contained 0.3 wt % water (Mitsubishi Moisture Meter CA06).

A solution of 29.9 g (0.100 mole) of the Formula V compound, 8-(2-pyrimidinyl)-8-aza-5-azoniaspiro[4.5]decane bromide in 300 mL methanol was passed downward through the resin bed at a rate of 2.5 mL/min. Additional methanol (about 300 mL) was passed until the pH to moistened indicator paper was 7. The column effluents were collected in an argon-purged flask charged with 14.1 g (0.1 00 mole) of 3,3-dimethylglutarimide (IV). The mixture was stirred magnetically. The resulting water-clear solution contained 0.22 wt % water and gave (after acidification with nitric acid) a negative silver nitrate test (no Br$^-$).

The methanol solution was concentrated by distillation at 20 mm Hg at <15° C. and 470 mL distillate was collected. Then 70 mL 4-methyl2-pentanone was added. An additional 60 mL solvent was distilled in vacuo. The mixture was further concentrated by distillation at 760 mm Hg; the temperature at the still head slowly rose to 108° C. Distillation was continued until the contents of the flask weighed 50 g. An additional 55 mL 4-methyl-2-pentanone was added. The suspension was stirred and heated at gentle reflux (head temperature 108°–110° C.) for 1.5 h. The mixture was filtered hot to remove a very small amount of insoluble material. This material was sodium 3,3-dimethylglutarimidate, probably resulting from an incomplete rinsing of sodium hydroxide from the resin column. The filtrate was reheated to boiling to dissolve the precipitated solid, and the clear, pale-yellow solution was allowed to cool slowly with stirring. The resulting mixture was stirred and chilled to 5° C. for 2 h. The solid was collected on a filter, rinsed with 30 mL cold 4-methyl- 2pentanone and dried at 50° C. (15 mm Hg) for 8 h. The off-white solid weighed 29.2 g (81.3% of theory). M.p. 107°–110° C. Hplc² HI 95.6 for gepirone.

EXAMPLE 7

N-[4-[4-(2-Pyrimidinyl)-1-piperazinyl]butyl]-2,3-norbornanedicarboximide, Tandospirone (I)

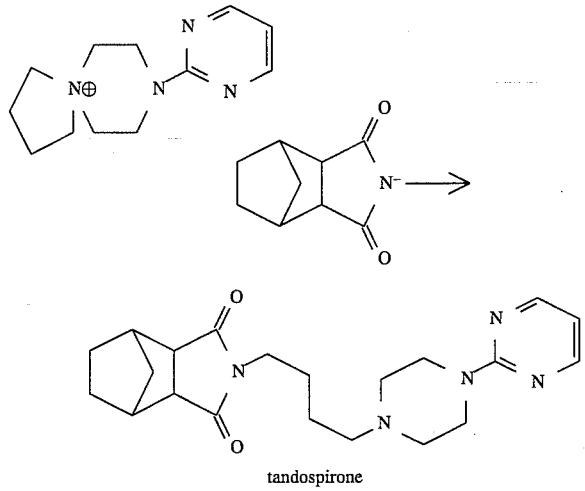

tandospirone

A solution of 119.5 mg (0.31 mmol) 8-(2-pyrimidinyl)-8-aza- 5azoniaspiro[4.5]decane, salt with (endo,endo)-bicyclo[2.2.1]heptane- 2,3-dicarboxylic acid imide (II, see Example 4) in 2 mL N,N-dimethylformamide was stirred and heated under an argon atmosphere at 130°–133° C. for 2.5 h. The solution was cooled to 25° C., and then it was diluted with 5 mL water. The mixture was extracted with 2×5 mL ethyl acetate. The extract was washed with 2 mL saturated sodium chloride solution, dried ($MgSO_4$), and then concentrated in vacuo at 23° C. to an oil. The oil was stored in vacuo at 50° C. for 18 h. The material had crystallized. The white solid weighed 118.0 mg (98.7 mol % of theory). The analytical data (ir, $^1H$ NMR, $^{13}C$ NMR and elemental analysis) were consistent for the assigned structure.

Calc. (found) for $C_{21}H_{29}N_5O_2$: C 65.77(65.62); H 7.62 (7.70); N 18.26 (18.01). $^1H$ NMR (200 MHz, $CDCl_3$) δ8.30 (d, J=6 Hz, 2H), 6.56 (t, J=4 Hz, 1H), 3.83 (t, 4H), 3.50(t, 2H), 3.08 (bs, 2H), 2.73 (s, 2H), 2.50 (t, 4H), 2.41 (t, 2H), 1.57 (m, 8H), 1.23 (d, 2H). $^{13}C$ NMR (50 MHz, $CDCl_3$) δ178.9, 162.1, 158.1, 110.1, 58.22, 53.19, 48,07, 43.67, 42.23, 39,28, 38.34, 25.98, 24.20.

The foregoing examples are intended only for illustration of the novel process. It will be apparent to those skilled in the art that the process can be modified in certain ways to produce the azapirone products, see, for example, the following procedures.

EXAMPLE 8

Synthesis of Gepirone from III and IV

A mixture of 0.30 g (1.25 mmole) of 8-(2-pyrimidinyl)-8-aza- 5azoniaspiro[4.5]decane hydroxide (III) and 0.18 g (1.25 mmole) of 3,3-dimethylglutarimide (IV) in 10 mL toluene was stirred and heated at gentle reflux with a water-trap under argon. All but a small amount of the material dissolved with time. After heating for 3 h, the mixture was cooled to 23° C. and filtered. The filtrate was concentrated in vacuo to give 0.44 g solid, which by hplc² was principally gepirone (HI 81.3).

EXAMPLE 9

Synthesis of Gepirone from II

The imidate salt (II) of Example 2 was converted to gepirone by heating in various solvents, and the results are tabulated below (Table 1). A detailed description is given here for the reaction in MIBK.

A slurry of 1.91 g (5.3 mmole) of Example 2 imidate) in 4 mL 4-methyl-2-pentanone (MIBK) was stirred under argon as the mixture was heated to gentle reflux. After 0.5 h at the boil, the mixture was checked by tlc³. Starting material $R_f$(0.0) and gepirone $R_f$(0.59) were observed. After 1 h the starting material was depleted. The reaction solution was cloudy and brown. It was chilled to 5° C., and the resulting tan solid was collected on a filter, rinsed with 1 mL cold MIBK and air-dried; the solid weighed 1.45 g (hplc HI 97.6 for gepirone). The combined filtrates were concentrated in vacuo to give 0.29 sticky solid (hplc HI 9.5 for the glutarimide IV and HI 85.8 for gepirone). It was recrystallized from MIBK to give 0.15 g tan solid. The combined total yield of gepirone was 1.60 g (83.8% of theory).

Calc. (found) for $C_{19}H_{29}N_5O_2$: C 63.48 (63.22), H 8.13 (8.21), N 19.48 (19.37). Ir, $^1H$ NMR and $^{13}C$ NMR consistent for assigned structure.

TABLE 1

| Conversion of Imidate Salt (II) to Gepirone in Various Solvents | | | | |
|---|---|---|---|---|
| Solvent | Temp °C. | Time, Hr | HI | Comments |
| IPA | 83 | 48, 50% conversion | 50 | Significant impurities |
| THF | 56 | 7, 100% conversion | 93 | Clean |
| MeCN | 82 | 24, 100% conversion | 74 | Clean |
| Toluene | 110 | 1, 100% conversion | 90 | Clean |
| NMP | 150 | 0.25, 100% conversion | 95 | 80% yield, 2 crops |
| MIBK | 117 | 1, 100% conversion | 98 | 83% yield, 2 crops |

I claim:

1. An improved process for preparing certain useful azapirones (I)

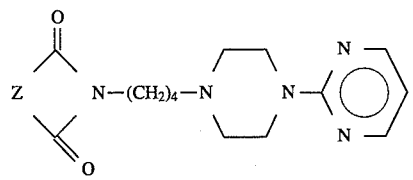

wherein Z is a member selected from the group consisting of

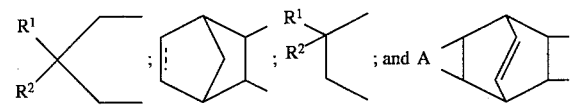

with $R^1$ and $R^2$ being independently selected from hydrogen and $C_{1-4}$ alkyl, or $R^1$ and $R^2$ can be taken together as a butanediyl or pentanediyl chain; the dotted and solid line representing either a single or a double chemical bond; and A being selected from the group consisting of O, $CH_2$, $CH_2CH_2$ and CH=CH;

which comprises a) reaction of 8-(2-pyrimidinyl)-8-aza- 5-azoniaspiro[4,5]decane hydroxide (III)

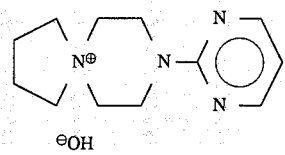

with an imide compound (IV)

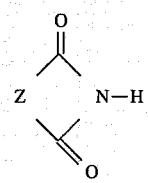

to produce an imidate salt compound (II); and

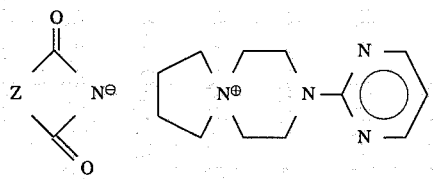

b) heating the imidate salt compound (II) to generate the azapirone product (I).

2. The process of claim 1 wherein Z is

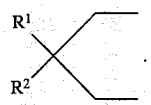

3. The process of claim 1 wherein Z is

4. The process of claim 1 wherein Z is

5. The process of claim 1 wherein Z is

6. The process of claim 2 wherein $R^1$ and $R^2$ are methyl.

7. The process of claim 2 wherein $R^1$ and $R^2$ are taken together as a butanediyl chain.

8. The process of claim 1 wherein salt compound II is heated in a nonreactive organic solvent.

9. The hydroxide intermediate III which is 8-(2-pyrimidinyl)-8-aza- 5-azoniaspiro[4,5]decane hydroxide.

10. The imidate salt (II)

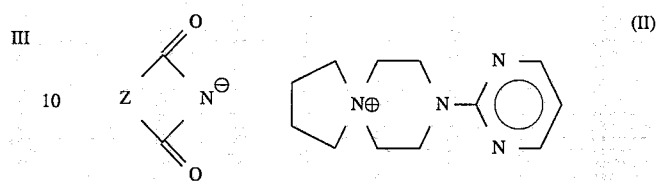

wherein Z is a member selected from the group consisting of

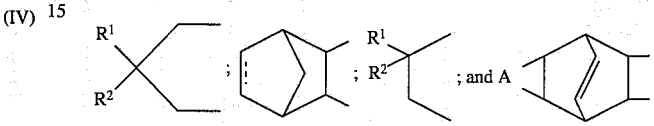

with $R^1$ and $R^2$ being independently selected from hydrogen and $C_{1-4}$ alkyl, or $R^1$ and $R^2$ can be taken together as a butanediyl or pentanediyl chain; the dotted and solid line representing either a single or a double chemical bond; and A being selected from the group consisting of O, $CH_2$, $CH_2CH_2$ and CH=CH.

11. The imidate salt of claim 10 wherein Z is

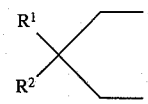

12. The imidate salt of claim 10 wherein Z is

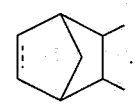

13. The imidate salt of claim 10 wherein Z is

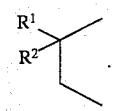

14. The imidate salt of claim 10 wherein Z is

15. The imidate salt of claim 11 wherein $R^1$ and $R^2$ are methyl.

16. The imidate salt of claim 11 wherein $R^1$ and $R^2$ are taken together as a butanediyl chain.

* * * * *